US012721716B2

(12) United States Patent
Song et al.

(10) Patent No.: US 12,721,716 B2
(45) Date of Patent: Sep. 1, 2026

(54) BILE DUCT STENT AND METHOD OF MANUFACTURING THE SAME

(71) Applicants: THE ASAN FOUNDATION, Seoul (KR); UNIVERSITY OF ULSAN FOUNDATION FOR INDUSTRY COOPERATION, Ulsan (KR); STANDARD SCI-TECH INC., Seoul (KR); SEWOON MEDICAL CO., LTD., Cheonan-si (KR)

(72) Inventors: Tae Jun Song, Seoul (KR); Jae Hee Lee, Seoul (KR)

(73) Assignees: THE ASAN FOUNDATION, Seoul (KR); UNIVERSITY OF ULSAN FOUNDATION FOR INDUSTRY COOPERATION, Ulsan (KR); STANDARD SCI-TECH INC., Seoul (KR); SEWOON MEDICAL CO., LTD., Cheonan-si (KR)

(*) Notice: Subject to any disclaimer, the term of this patent is extended or adjusted under 35 U.S.C. 154(b) by 1036 days.

(21) Appl. No.: 17/840,626

(22) Filed: Jun. 15, 2022

(65) Prior Publication Data

US 2022/0304796 A1 Sep. 29, 2022

Related U.S. Application Data

(63) Continuation of application No. PCT/KR2021/004125, filed on Apr. 2, 2021.

(30) Foreign Application Priority Data

Apr. 17, 2020 (KR) ........................ 10-2020-0046815

(51) Int. Cl.

| | |
|---|---|
| ***A61F 2/04*** | (2013.01) |
| ***A61F 2/90*** | (2013.01) |
| *A61F 2/01* | (2006.01) |

(52) U.S. Cl.

CPC .................. *A61F 2/04* (2013.01); *A61F 2/90* (2013.01); *A61F 2/0105* (2020.05);

(Continued)

(58) Field of Classification Search

CPC .......... A61F 2002/041; A61F 2230/005; A61F 2/0105; A61F 2/2475

(Continued)

(56) References Cited

U.S. PATENT DOCUMENTS

| | | | | |
|---|---|---|---|---|
| 7,041,126 | B2 * | 5/2006 | Shin .......................... | A61F 2/07 623/1.51 |
| 2008/0223476 | A1 | 9/2008 | Stinson | |
| 2014/0379092 | A1 | 12/2014 | Kawasumi et al. | |

FOREIGN PATENT DOCUMENTS

| | | | |
|---|---|---|---|
| KR | 100170220 | B1 | 3/1999 |
| KR | 1020040021266 | A | 3/2004 |

(Continued)

OTHER PUBLICATIONS

Translation of KR 20190014335 (Year: 2019).*

(Continued)

*Primary Examiner* — Brian E Pellegrino
(74) *Attorney, Agent, or Firm* — Nicholas Park

(57) ABSTRACT

A bile duct stent and a method of manufacturing the same are disclosed. The bile duct stent having a backflow preventing means according to an embodiment of the present invention includes: a cylindrical body having a mesh structure formed by zigzagging metal wires of a shape memory alloy on a plurality of pins each disposed in a circumferential direction X and a longitudinal direction Y of a cylindrical jig; a film portion coated on cells of the metal wires of the mesh structure; and a backflow-preventing pattern film in which a hole is formed in the film portion of each cell formed at an outlet end of the cylindrical body and threads (Continued)

(Lasso) fixed by zigzagging to the cells of the metal wires in the circumferential direction by passing through any one hole (h) cross the outlet end one time or more to form a network structure.

2 Claims, 13 Drawing Sheets

(52) U.S. Cl.
CPC . *A61F 2002/041* (2013.01); *A61F 2210/0014* (2013.01); *A61F 2230/005* (2013.01)

(58) Field of Classification Search
USPC ........................................................ 623/1.51
See application file for complete search history.

(56) References Cited

FOREIGN PATENT DOCUMENTS

| | | |
|---|---|---|
| KR | 1020100094763 A | 8/2010 |
| KR | 1020140094144 A | 7/2014 |
| KR | 1020190014335 A | 7/2019 |
| WO | 2013115141 A1 | 8/2013 |

OTHER PUBLICATIONS

WIPO, ISA210, International Search Report of International Application No. PCT/KR2021/004125, Jul. 28, 2021, 5 pages.
WIPO, ISA237, International Written Opinion of International Application No. PCT/KR2021/004125, Jul. 28, 2021, 5 pages.

* cited by examiner

FIG. 5

(Start, End)
13#1
(A)

(Start, End)
13#2
(B)

(Start, End)
13#3
(B)

(Start, End)
13#3'
(D)

(Start, End)
13#4
(E)

(Start, End)
13#5
(F)

BILE DUCT STENT AND METHOD OF MANUFACTURING THE SAME

CROSS-REFERENCE TO RELATED APPLICATION

This application is a US Bypass Continuation Application of International Application No. PCT/KR2021/004125, filed on Apr. 2, 2021, and designating the United States, the International Application claiming a priority date of Apr. 17, 2020, based on prior Korean Application No. 10-2020-0046815, filed on Apr. 17, 2020, the disclosure of which is incorporated herein by reference in its entirety.

BACKGROUND

Technical Field

The present invention relates to a bile duct stent and a method of manufacturing the same, and more particularly, to a bile duct stent for preventing the backflow of food in the duodenum and a method of manufacturing the same.

Background Art

Generally, a bile duct serves as a passage that allows bile, which is concentrated after being produced by the liver and stored in the gallbladder, to flow to the duodenum. A biliary stricture is a disease in which the bile duct is constricted and the passage is narrowed or blocked due to tumors such as pancreatitis/pancreatic cancer and cholangitis/cholangiocarcinoma.

A biliary stricture can be treated with surgery, but endoscopic biliary stenting has been used in recent years. In particular, stenting is widely practiced when surgery is not possible due to the onset of a malignant biliary stricture in terminal cancer patients.

However, regarding the conventional bile duct stent, a problem has been pointed out in that food passing through the duodenum frequently flows back into the bile duct, obstructing the flow of bile and causing side effects due to cholangitis or stent malfunction.

In order to address such a problem, a bile duct stent having a backflow preventing means has been proposed in the past, but it is difficult to prove its effectiveness due to various shortcomings.

For example, Korean Patent Registration No. 0170220 discloses a stent having a backflow preventing means formed of tricuspid valve/tricuspid valve type valves made of a resin material.

However, the valves disclosed in Korean Patent Registration No. 0170220 have a disadvantage in that, when an expansile force of the stent is weak or when the stent does not maintain a sufficiently expanded state, openings of the valves are not sufficiently opened and reach a closed state, thus obstructing the supply of bile and causing solidification of stagnant bile. In addition, since the backflow preventing means is made of a resin material, there is a disadvantage in that durability is lowered due to an occurrence of film damage caused by bile as in the conventional tubular stent.

Therefore, there is a need for ways to address the conventional backflow prevention problem and secure durability to expand the effects of stent placement in the bile duct.

Matters described in the "Background Art" section are intended to enhance understanding of the background of the invention and may include matters that are not related art already known to those of ordinary skill in the art to which the present invention pertains.

SUMMARY

Technical Problem

Embodiments of the present invention are directed to providing a bile duct stent, in which a backflow-preventing pattern film utilizing a pattern member made of threads (Lasso) or metal wires is formed at a duodenum-side outlet of the stent, which is inserted into the bile duct, to prevent food in the duodenum from flowing back into the bile duct, and a method of manufacturing the same.

Technical Solution

One aspect of the present invention provides a bile duct stent having a backflow preventing means, the bile duct stent including: a cylindrical body having a mesh structure formed by zigzagging metal wires of a shape memory alloy on a plurality of pins each disposed in a circumferential direction X and a longitudinal direction Y of a cylindrical jig; a film portion coated on cells of the metal wires of the mesh structure; and a backflow-preventing pattern film in which a hole is formed in the film portion of each cell formed at an outlet end of the cylindrical body and threads (Lasso) fixed by zigzagging to the cells of the metal wires in the circumferential direction by passing through any one hole (h) cross the outlet end one time or more to form a network structure.

Also, another aspect of the present invention provides a bile duct stent having a backflow preventing means, the bile duct stent including: a cylindrical body having a mesh structure formed by zigzagging metal wires of a shape memory alloy on a plurality of pins each disposed in a circumferential direction X and a longitudinal direction Y of a cylindrical jig; and a backflow-preventing pattern film in which the metal wires are woven on a pin P and another pin P disposed in the circumferential direction X at a lower end of the jig and the metal wires cross an outlet end of the cylindrical body one time or more to form a network structure.

The backflow-preventing pattern film may be formed as any one of a cross-shaped backflow-preventing pattern film, a straight backflow-preventing pattern film, a zigzag-shaped backflow-preventing pattern film, a polygonal backflow-preventing pattern film, and a star-shaped backflow-preventing pattern film in which the metal wires cross the outlet end and intersect each other.

Also, the backflow-preventing pattern film may be finished with a twist knot after one line of metal wires is continuously woven from a start-point pin P to an end-point pin P via at least one pin P.

Also, as the cross-shaped backflow-preventing pattern film, one line of metal wires may be knotted by twisting at least once or more after a first line crossing the center of the outlet end from a first pin P1, which is a start point, is woven on a second pin, extends and moves 90° in the circumferential direction, and is woven on a third pin, and then a second line crossing the outlet end from the third pin vertically intersects the first line and is woven on a fourth pin, which is an end point.

Also, the backflow-preventing pattern film may be formed as a radial backflow-preventing pattern film by sequentially weaving the metal wires on pins P disposed in the circumferential direction X at a lower end of the jig and a single vertical pin Py disposed at the center of a lower surface of the jig.

Also, in the radial backflow-preventing pattern film, multiple lines of metal wires woven on the vertical pin Py may be fixed by intersecting each other in a bent state.

Also, the backflow-preventing pattern film may be formed as a conical backflow-preventing pattern film in which an inclined outer peripheral surface having a conical shape is formed at a lower surface of the jig, the vertical pin Py is fixed to a vertex at the center of the outer peripheral surface, the metal wires are sequentially woven between the vertical pin Py and the pins P, which are disposed in the circumferential direction X at the lower end of the jig, to form a radial pattern, and the center protrudes due to the inclined outer peripheral surface having the conical shape.

Also, the conical backflow-preventing pattern film may form a triangular structure as bent portions caused by the vertical pin Py are formed on the metal wire lines constituting the radial pattern and may form an inclined structure in which the bent portions intersect and radiate while interfering with each other.

Also, the backflow-preventing pattern film may be formed as a radial backflow-preventing pattern film in which a circular array of vertical pins is formed around the center of the lower surface of the jig, and the pins P disposed in the circumferential direction X at the lower end and the array of vertical pins Py each corresponding to the pins P are sequentially woven.

Also, the backflow-preventing pattern film may be formed as a truncated conical backflow-preventing pattern film in which a truncated cone outer peripheral surface, which is inclined, and a truncated cone lower surface are formed at the lower end of the jig to constitute a shape that is broad at the top and gets narrower toward the bottom, a circular array of the vertical pins Py is formed around the center of the truncated cone lower surface, and the pins P disposed in the circumferential direction and the array of the vertical pins Py each corresponding to the pins P are sequentially woven using the metal wires.

Also, in the truncated conical backflow-preventing pattern film, a bent portion caused by the vertical pin Py may be formed on each metal wire line, and the bent portions may form an inclined structure in which the lines radiate without interfering with each other.

Meanwhile, one aspect of the present invention provides a method of manufacturing a bile duct stent using a jig, the method including: a) forming a cylindrical body having a mesh structure by zigzagging metal wires of a shape memory alloy material on a plurality of pins each disposed in a circumferential direction X and a longitudinal direction Y of a cylindrical jig; and b) forming a backflow-preventing pattern film having a network structure by causing a pattern member made of threads (Lasso) or metal wires to cross an outlet end of a passage of the cylindrical body one time or more.

Also, the step b) may include forming a conical backflow-preventing pattern film in which a lower surface of the jig, which has an inclined outer peripheral surface having a conical shape and the vertical pin Py fixed to a vertex at the center of the outer peripheral surface, and the pins P, which are disposed in the circumferential direction X at the lower end of the jig, are sequentially woven using the metal wires to form a radial pattern, and the center protrudes due to the inclined outer peripheral surface having the conical shape.

In addition, the step b) may include: a step in which the metal wire is woven from a first pin P1, which is a start point, to the vertical pin Py at the center to form a bent portion, is woven on a second pin, and then extends and moves to a third pin in a circumferential direction; a step in which the metal wire is woven from the third pin to the vertical pin Py at the center to form a bent portion, is woven on a fourth pin, and then extends and moves to a fifth pin in the circumferential direction; and a step in which the metal wire is woven from the fifth pin to the vertical pin Py at the center to form a bent portion, is woven on a sixth pin which is an end point, and then is knotted by twisting at least once or more.

BRIEF DESCRIPTION OF THE DRAWINGS

FIG. 5 illustrates an example of implementing various backflow-preventing pattern films using the threads according to the first embodiment of the present invention.

DETAILED DESCRIPTION

Modes of the Invention

Figure 1:
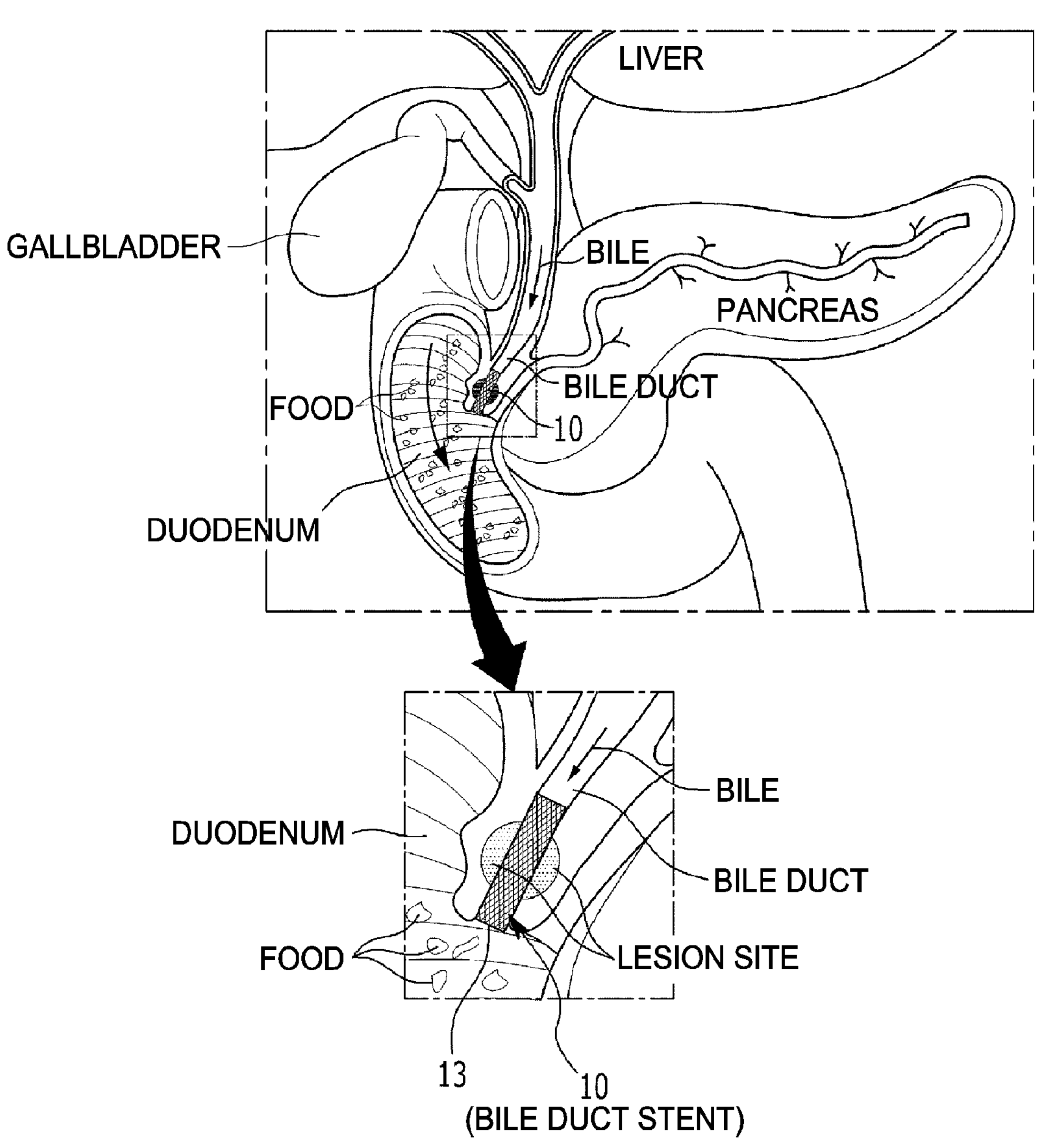
FIG. 1 is a conceptual diagram illustrating a state in which a bile duct stent according to an embodiment of the present invention is placed.

Hereinafter, embodiments of the present invention will be described in detail with reference to the accompanying drawings to allow those of ordinary skill in the art to which the present invention pertains to easily carry out the invention. However, the present invention may be implemented in various different forms and is not limited to the embodiments described herein. Also, in the drawings, parts unrelated to the description have been omitted to clearly describe the present invention, and like parts are denoted by like reference numerals throughout the specification.

Throughout the specification, when a certain part is described as "including" a certain element, unless otherwise stated, this does not exclude the inclusion of other elements but in fact the certain part may further include other elements. Also, terms such as "portion," "-er/or," and "module" indicate units of processing at least one function or operation.

Throughout the specification, terms such as "first" or "second" may be used to describe various elements, but the elements are not limited by the terms. The terms are only used for the purpose of distinguishing one element from another element. For example, without departing from the scope of rights according to the concept of the present invention, a first element may be referred to as a second element, and likewise, a second element may also be referred to as a first element.

Now, a bile duct stent and a method of manufacturing the same according to embodiments of the present invention will be described in detail with reference to the drawings.

FIG. 1 is a conceptual diagram illustrating a state in which a bile duct stent according to an embodiment of the present invention is placed.

Referring to FIG. 1, a state in which a bile duct stent 10 according to an embodiment of the present invention is inserted into the bile duct connected to the duodenum is shown.

The bile duct stent 10 has a cylindrical mesh structure formed using metal wires and has self-elasticity and thus contracts when an external force is applied thereto and expands when the external force is removed.

Through stenting, the bile duct stent 10 is inserted into a luminal lesion site where a biliary stricture has occurred. The bile duct stent 10 expands a lumen by its self-expansile force and maintains the lumen in an expanded state so that the lumen is not narrowed again, and in this way, the bile duct stent 10 serves to facilitate the flow of bile in the duodenum.

In the previous description, it has been pointed out that, in the conventional stent structure, food passing through the duodenum may flow back into the expanded bile duct, and when the food flows back into the stent, the flow of bile may be obstructed and various problems may occur.

Thus, embodiments of the present invention are directed to providing a bile duct stent, in which a backflow-preventing pattern film is formed by weaving a pattern member made of threads (Lasso) or metal wires with a duodenum-side outlet end that is inserted into the bile duct to prevent the backflow of food from the duodenum into the bile duct, and a method of manufacturing the same.

Hereinafter, in describing the bile duct stent and the method of manufacturing the same according to the present invention, a stent with a backflow-preventing pattern film of various patterns according to the type of the pattern member and a method of manufacturing the same will be described in detail below according to various embodiments.

First, a stent with a backflow-preventing pattern film using threads and a method of manufacturing the same will be described according to a first embodiment of the present invention.

First Embodiment

Figure 2:
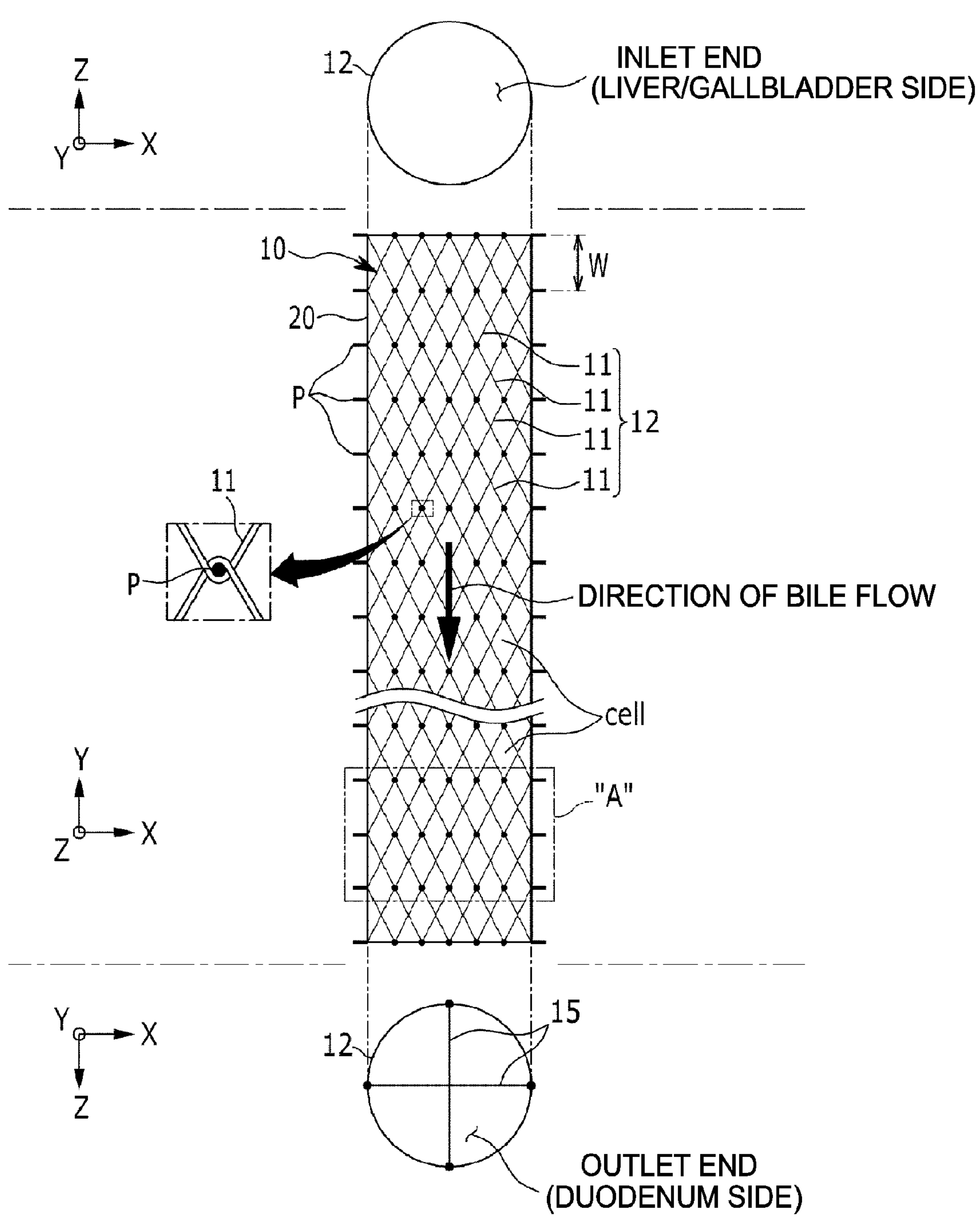
FIG. 2 illustrates a state in which a bile duct stent is manufactured using a jig according to a first embodiment of the present invention.

FIG. 2 illustrates a state in which a bile duct stent is manufactured using a jig according to a first embodiment of the present invention.

Referring to FIG. 2, a bile duct stent 10 (hereinafter referred to as "stent" for convenience) according to the first embodiment of the present invention is manufactured by zigzagging metal wires 11 on a plurality of pins P disposed in a circumferential direction X and a longitudinal direction Y of a cylindrical jig 20.

The stent 10 may be manufactured to have a cylindrical body 12 whose diameter is in a range of 8 mm to 10 mm and a length is in a range of 5 cm to 7 cm, but the stent 10 is not limited thereto and may be made to order by extending the length of the jig 20 according to the size of a lesion site of a patient.

The metal wires 11 may be made of a shape memory alloy such as nitinol to allow a certain expansile force to act at a certain temperature as in the lumen of the bile duct, but other known stent-manufacturing wires may be utilized as the metal wires 11.

The metal wires 11 form zigzag patterns by being woven in the circumferential direction X in which the plurality of pins P are disposed at certain intervals, and the stent 10 having the cylindrical body 12 having a mesh structure in which the zigzag patterns formed in the circumferential direction X intersect each other while interfering with each other and are arranged at predetermined intervals W in the longitudinal direction Y is manufactured. The cylindrical mesh structure of the stent 10 is shown as having a shape in which rhombic patterns, each with all four sides the same length, are arranged in the circumferential direction X and the longitudinal direction Y of the stent 10.

Figure 3:
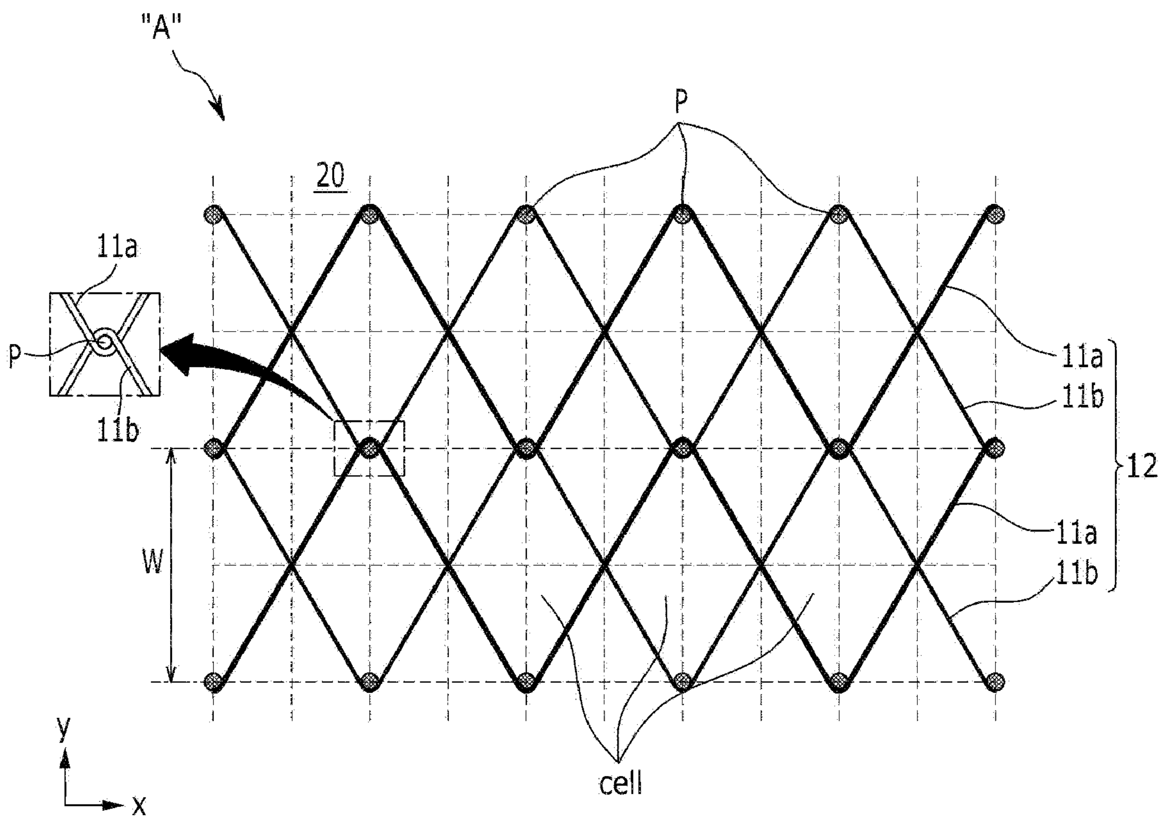
FIG. 3 is a development view illustrating a weaving structure of a stent body according to the first embodiment of the present invention.

For example, FIG. 3 is a development view illustrating a weaving structure of a stent body according to the first embodiment of the present invention.

The metal wires 11 according to the embodiment of the present invention include first metal wires 11*a* and second metal wires 11*b* each of which is able to contract and expand by itself, has flexibility, and is formed to have a unit length.

Referring to FIG. 3, a state in which zigzag patterns of the first metal wires 11*a* and the second metal wires 11*b* are woven while interfering with each other to form rhombic patterns and are each rotated twice is shown.

Here, vertical intersection points of a checkerboard shape formed by dotted lines are positions of holes H where the pins P are inserted into the jig 20, and round points at the intersection points indicate a state in which the pins P are installed in the holes H. In the state in which the pins P are disposed in the jig 20, the first metal wires 11*a* and the second metal wires 11*b* are woven to manufacture the cylindrical body 12 having the mesh structure.

Also, the first metal wires 11*a* and the second metal wires 11*b* are configured to be bent due to the pins P and to only intersect each other without being twisted. In this way, flexibility can be secured, and an easily collapsible structure can be secured upon loading on a catheter afterwards.

A passage of the cylindrical body 12 is directed according to a direction in which bile flows in the bile duct, and an upper end of the passage that is formed at the liver or gallbladder side is defined as an inlet end (IN) while a lower end of the passage that is formed at the duodenum side is defined as an outlet end (OUT).

Here, in the stent 10 according to the first embodiment of the present invention, a backflow-preventing pattern film 13 formed of a network structure using nylon threads (Lasso) 15 is formed at the duodenum-side outlet end (OUT) of the cylindrical body 12 that is inserted into the bile duct, and in this way, the backflow of food from the duodenum into the bile duct is prevented.

The overall process of manufacturing the stent 10 according to the first embodiment of the present invention includes a step in which the metal wires 11 are woven through the jig 20 and then heat-treated to form the cylindrical body 12 having elasticity, a step in which the cylindrical body 12 separated from the jig 20 is fitted to a film jig (not illustrated) and coated with a silicone coating solution and then dried to form a silicone film portion 14, and a step in which the threads 15 are woven to the outlet end of the cylindrical body 12 to manufacture the backflow-preventing pattern film 13 having a network structure.

Figure 4:
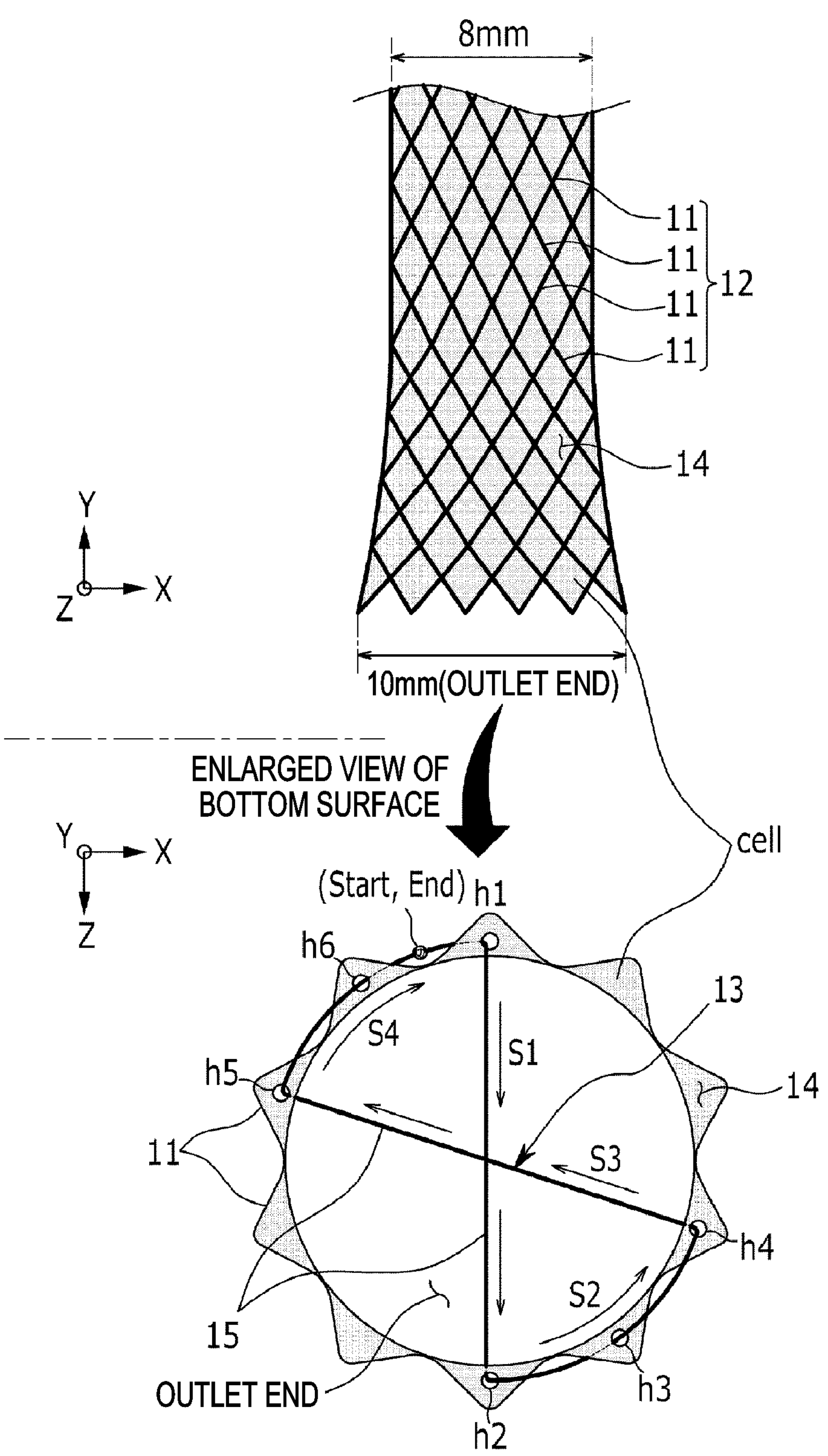
FIG. 4 illustrates an example of manufacturing a cross-shaped backflow-preventing pattern film using threads according to the first embodiment of the present invention.

For example, FIG. 4 illustrates an example of manufacturing a cross-shaped backflow-preventing pattern film using threads according to the first embodiment of the present invention.

Referring to FIG. 4, the stent 10 according to the first embodiment of the present invention may be manufactured so that a diameter of the outlet end of the cylindrical body (e.g., 10 mm) is greater than a diameter of the central portion thereof (e.g., 8 mm). FIG. 4 shows a state in which the silicone film portion 14 is formed on the cylindrical body 12. Here, from an enlarged view of the bottom surface of the outlet end of the cylindrical body 12, it can be seen that cells made of the metal wires 11 are arranged in a circular shape about the center like petals of a sunflower.

Here, a hole h is formed in the silicone film portion 14 of each cell formed at the outlet end of the cylindrical body 12.

The backflow-preventing pattern film 13 may be formed to have a network structure by repeating a process in which the thread 15 fixed by zigzagging to the cell made of the metal wires 11, which is formed in the circumferential direction through any one hole h at a start point, crosses the outlet end one time or more, and passes through another hole h.

For example, looking at the process of manufacturing the cross-shaped backflow-preventing pattern film 13 in detail with reference to FIG. 4, the thread 15 passes through a first hole h1 from a start point (Start) and then crosses the outlet end and passes through a second hole h2 (S1), passes through a third hole h3 of a cell made of the metal wires 11, which is formed in the circumferential direction, to be woven to another thread 15 so that the threads 15 interfere with each other (S2), passes through a fourth hole h4 and then crosses the outlet end and passes through a fifth hole h5 (S3), then passes through a sixth hole h6, which is formed in the circumferential direction, and then is knotted at an end point (End) (S4).

In this way, with one task, the thread 15 may sequentially pass through the holes h of the silicone film portion 14, which is formed on each cell, from the start point (Start) and be woven as if stitched to the cells made of the metal wires 11 to form the cross-shaped backflow-preventing pattern film 13 at the outlet end and then may be knotted at the end point (End) which is the same as the start point (Start).

Meanwhile, the backflow-preventing pattern film 13 according to the first embodiment of the present invention is not limited to the cross-shaped backflow-preventing pattern film 13 described above, and backflow-preventing patterns of various other forms may be applied.

Figure 5:
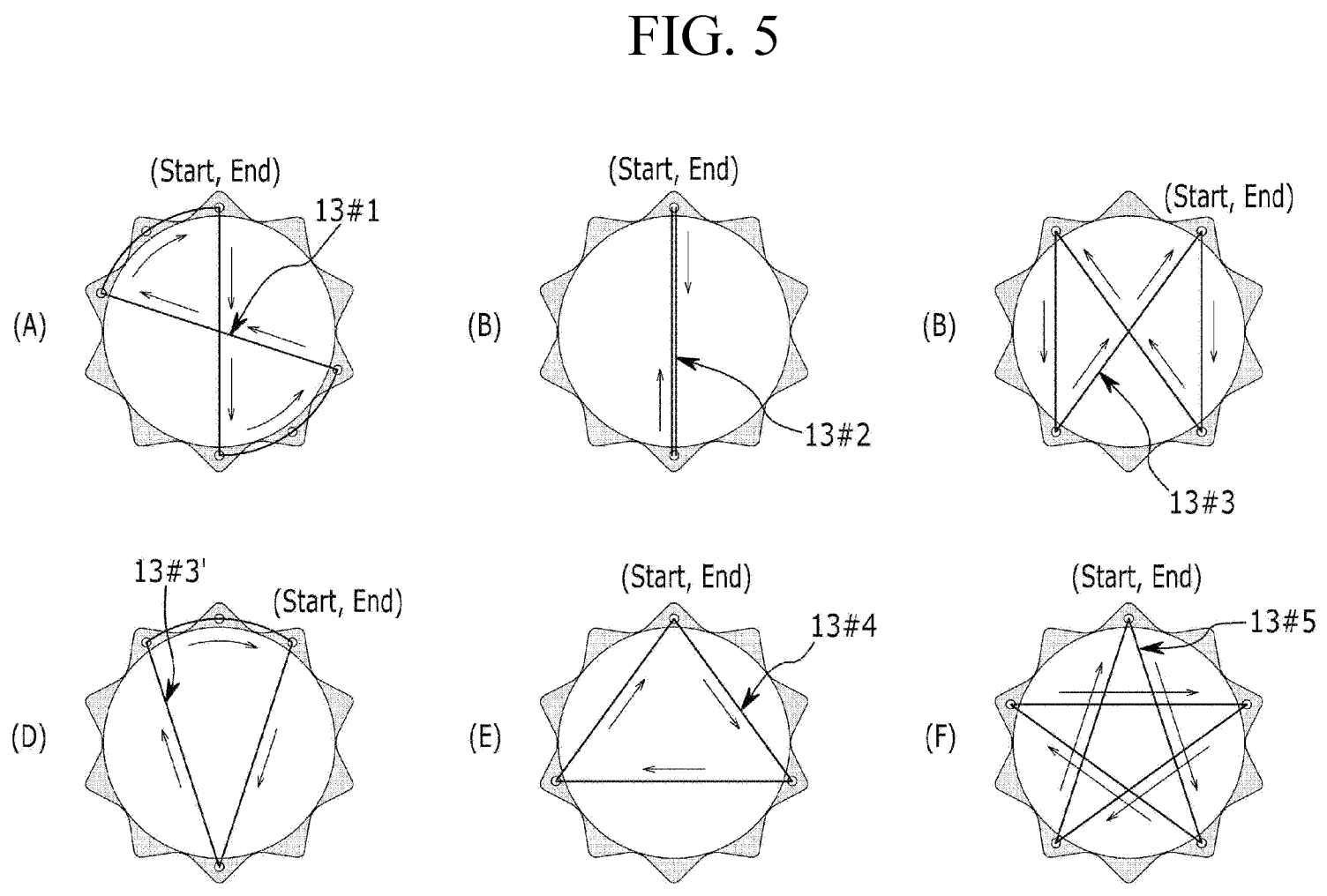

For example, FIG. 5 illustrates an example of implementing various backflow-preventing pattern films using the threads according to the first embodiment of the present invention.

Referring to FIG. 5, hereinafter, since backflow-preventing patterns #n according to various embodiments may be applied to the backflow-preventing pattern film 13 according to the embodiment of the present invention, like "13#*n*," the reference numeral of the backflow-preventing pattern film 13 and the reference numeral of the backflow-preventing pattern #n will be combined to distinguish the backflow-preventing pattern films 13 having different patterns.

That is, in addition to the above-described cross-shaped backflow-preventing pattern film 13#1, the backflow-preventing pattern film 13 may be formed as backflow-preventing pattern films 13 having various other patterns such as a straight backflow-preventing pattern film 13#2, a zigzag-shaped backflow-preventing pattern film 13#3, a V-shaped backflow-preventing pattern film 13#3', a polygonal backflow-preventing pattern film 13#4, and a star-shaped backflow-preventing pattern film 13#5 in which the thread 15 is woven between a hole h and another hole h and crosses the outlet end.

In this way, the stent 10 according to an embodiment of the present invention may be manufactured to have various backflow-preventing pattern films 13 according to ways in which the thread 15 is utilized and woven to the outlet end (OUT) of the cylindrical body 12. During placement of the stent 10, in a state in which the stent 10 is developed at a lesion site in the bile duct, the thread 15 forms a network structure of the backflow-preventing pattern. In this way, the stent 10 has an effect of preventing the backflow of food from the duodenum into the bile duct.

Also, the backflow-preventing pattern film 13 may be manufactured by stitching and weaving the thread 15 with a needle passing through the silicone film portion 14 formed on the periphery of the outlet end.

Since the backflow-preventing pattern film 13 is manufactured using threads, the stent 10 can be easily loaded on a catheter without difficulty of reducing the diameter of the stent 10, and since, during placement of the stent 10, the stent 10 is unfolded especially to have a pattern simultaneously as the cylindrical body 12 develops at a lesion site of the bile duct, the stent 10 has an effect of preventing the backflow of food from the duodenum into the bile duct.

Meanwhile, the pattern member of the backflow-preventing pattern film 13 of the stent 10 according to the embodiment of the present invention can be manufactured by utilizing the metal wires 11 as well as the threads 15, and a method of manufacturing the backflow-preventing pattern film 13 using the metal wires 11 will be described in detail below according to another embodiment.

Second Embodiment

Figure 6:
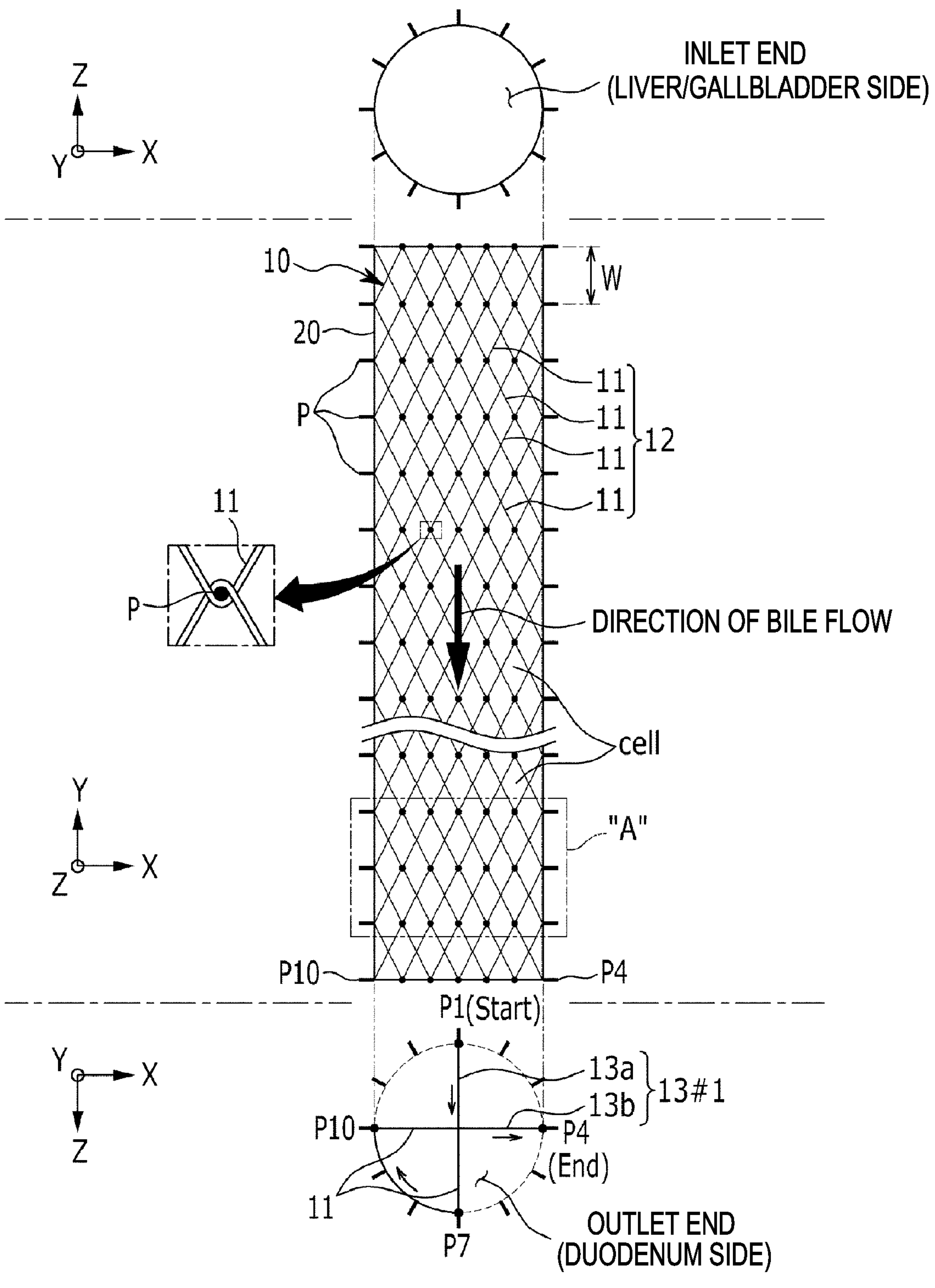
FIG. 6 illustrates a state in which a bile duct stent is manufactured using a jig according to a second embodiment of the present invention.

FIG. 6 illustrates a state in which a bile duct stent is manufactured using a jig according to a second embodiment of the present invention.

Hereinafter, since structures of a jig 20 and a stent 10 manufactured according thereto according to the second embodiment of the present invention are similar to those in the first embodiment described above, overlapping description will be omitted, and differences from the first embodiment will be mainly described.

Referring to FIG. 6, in the stent 10 according to the second embodiment of the present invention, a backflow-preventing pattern film 13 using metal wires 11 is formed at the duodenum-side outlet end (OUT) of the cylindrical body 12 that is inserted into the bile duct, and in this way, the backflow of food from the duodenum into the bile duct is prevented.

The overall process of manufacturing the stent 10 according to the second embodiment of the present invention is different from that according to the first embodiment in that, in a state in which the metal wires 11 are woven through the jig 20 to form the cylindrical body 12, the backflow-preventing pattern film 13 using the metal wires 11 is formed at the outlet end (OUT) and then heat-treated so that the cylindrical body 12 having elasticity and the backflow-preventing pattern film 13 are simultaneously manufactured. Then, the cylindrical body 12 of the stent 10 that is separated from the jig 20 is fitted to a silicone film jig (not illustrated) and coated with a coating solution and then dried to complete the manufacturing process.

The backflow-preventing pattern film 13 may be formed as the cross-shaped backflow-preventing pattern film 13#1 in which the metal wires 11 are woven between a pin P and another pin P, which are disposed in the circumferential direction X at one end (that is, a lower end) of the jig 20, and cross the outlet end (OUT) and intersect each other. Here, pins P1 to P12 disposed in the circumferential direction X at the lower end of the jig 20 are almost collinear with the outlet end at the one end surface.

Specifically, in order to form the cross-shaped backflow-preventing pattern film 13#1, the metal wires 11 are knotted by twisting at least once or more after a first line 13*a* crossing the outlet end from a first pin P1, which is a start point (Start), is woven on a seventh pin P7 and extends and moves 90° to a tenth pin P10 in the circumferential direction X, and then a second line 13*b* crossing the outlet end (OUT) from the tenth pin P10 vertically intersects the first line 13*a* and is woven on a fourth pin P4, which is an end point (End). In the above process, the metal wires 11 may be twisted one time or more with the metal wire 11 forming the outlet end when being woven on each pin P and may be fixed to interfere with each other.

In this way, by one line of the metal wires 11 being continuously woven from the first pin P1, which is the start point (Start), to the fourth pin P4, which is the end point (End), and then being finished with a twist knot to another line, the backflow-preventing pattern film 13 can be easily manufactured. Further, since it is possible to first manufacture the cylindrical body 12 from the inlet end (IN) to the outlet end (OUT) through the jig 20 and then form the backflow-preventing pattern film 13 using the metal wires 11 at the outlet end (OUT) without a pause, there is an advantage in that the manufacturing process is reduced.

When the task of weaving the metal wires 11 to the backflow-preventing pattern film 13 is completed on the jig 20 as described above, the stent 10 may be separated from the jig 20 and undergo washing and sterilizing processes and then may be shipped out as a finished product. Here, a process of coating the cylindrical body 12 with a coating material and forming the film portion 14 may be further performed on the stent 10, and then the stent 10 may be shipped out as a covered-type metal stent product. The film portion 14 may be formed by coating the cylindrical body 12 with a coating solution such as polyurethane in a state in which the stent 10 is heated to a certain temperature.

Meanwhile, the backflow-preventing pattern film 13 using the metal wires 11 according to the second embodiment of the present invention is not limited to the cross-shaped backflow-preventing pattern film 13#1 described above, and backflow-preventing patterns of various other forms may be applied.

Figure 7A:
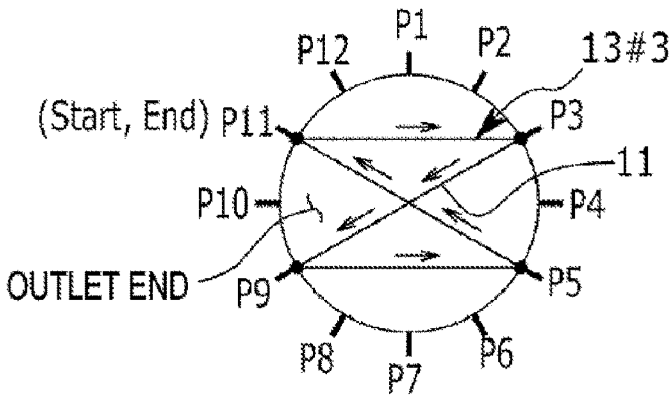
FIGS. 7A, 7B and 7C illustrate an example of implementing various backflow-preventing pattern films using metal wires according to the second embodiment of the present invention.
Figure 7B:
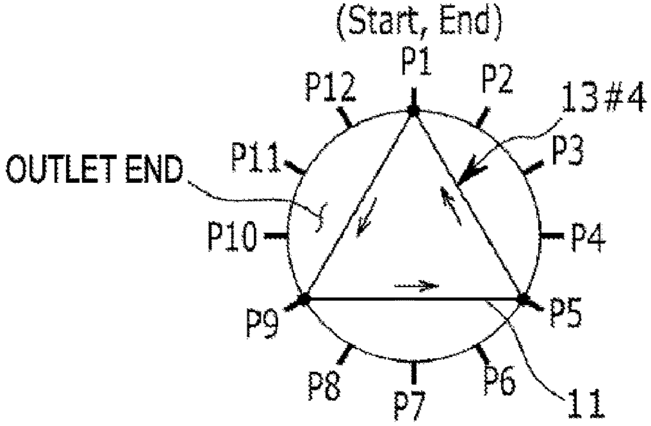
Figure 7C:
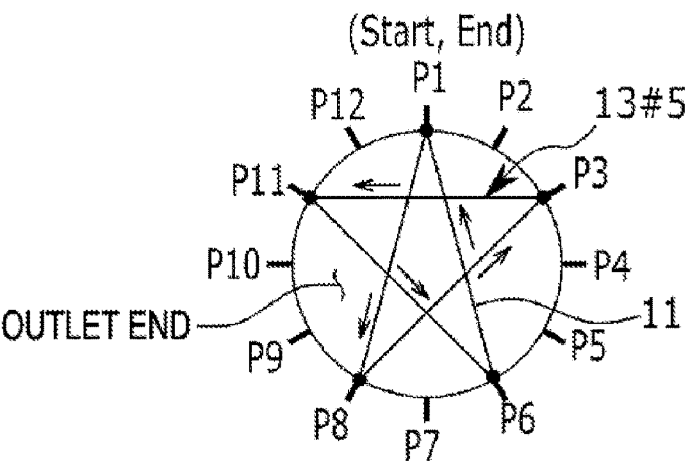

For example, FIGS. 7A, 7B and 7C illustrate an example of implementing various backflow-preventing pattern films using metal wires according to the second embodiment of the present invention.

Referring to FIGS. 7A, 7B and 7C, the backflow-preventing pattern film 13 according to the second embodiment of the present invention is not limited to the cross-shaped backflow-preventing pattern film 13#1 and may also be formed as the zigzag-shaped backflow-preventing pattern film 13#3, the polygonal backflow-preventing pattern film 13#4, and the star-shaped backflow-preventing pattern film 13#5 in which the metal wire 11 is woven between a pin P and another pin P and crosses the outlet end.

Referring to FIG. 7A, the zigzag-shaped backflow-preventing pattern film 13#3 may be formed by the metal wire 11 being knotted after crossing the outlet end from an eleventh pin P11, which is a start point (Start), and being woven on a third pin P3, and then sequentially crossing the outlet end and being woven on a ninth pin P9, crossing the outlet end and being woven on a fifth pin P5, and crossing the outlet end and being woven on the eleventh pin P11, which is an end point (End). The start point (Start) and the end point (End) are the same.

Referring to FIG. 7B, a triangular backflow-preventing pattern film may be formed by the metal wire 11 being knotted after crossing the outlet end from the first pin P1, which is a start point (Start), and being woven on the ninth pin P9, and then sequentially crossing the outlet end and being woven on the fifth pin P5, and crossing the outlet end and being woven on the first pin P1, which is an end point (End). Here, the polygonal backflow-preventing pattern film 13#4 may be formed in various other polygonal shapes such as a quadrangular shape in addition to being formed in a triangular shape, and the start point (Start) and the end point (End) are the same.

Referring to FIG. 7C, the star-shaped backflow-preventing pattern film 13#5 may be formed by the metal wire 11 being knotted after crossing the outlet end from the first pin P1, which is the start point (Start), and being woven on an eighth pin P8, and then sequentially crossing the outlet end and being woven on the third pin P3, crossing the outlet end and being woven on the eleventh pin P11, crossing the outlet end and being woven on a sixth pin P6, and crossing the outlet end and being woven on the first pin P1, which is the end point (End).

In addition, the stent 10 according to the embodiment of the present invention may be manufactured to have various backflow-preventing pattern films 13 according to ways in which the jig 20 is utilized and the metal wire 11 is woven to the outlet end (OUT) of the cylindrical body 12. Also, during placement of the stent 10, in a state in which the stent 10 is developed at a lesion site in the bile duct, the stent 10 has an effect of, by the backflow-preventing pattern film 13, preventing the backflow of food from the duodenum into the bile duct.

Meanwhile, the stent 10 may be manufactured to have a denser backflow-preventing pattern film 13 with an increase in the number of lines of the metal wire 11 that connect a pin P and another pin P and cross the outlet end (OUT). This will be described next according to a third embodiment.

Third Embodiment

Figure 8:
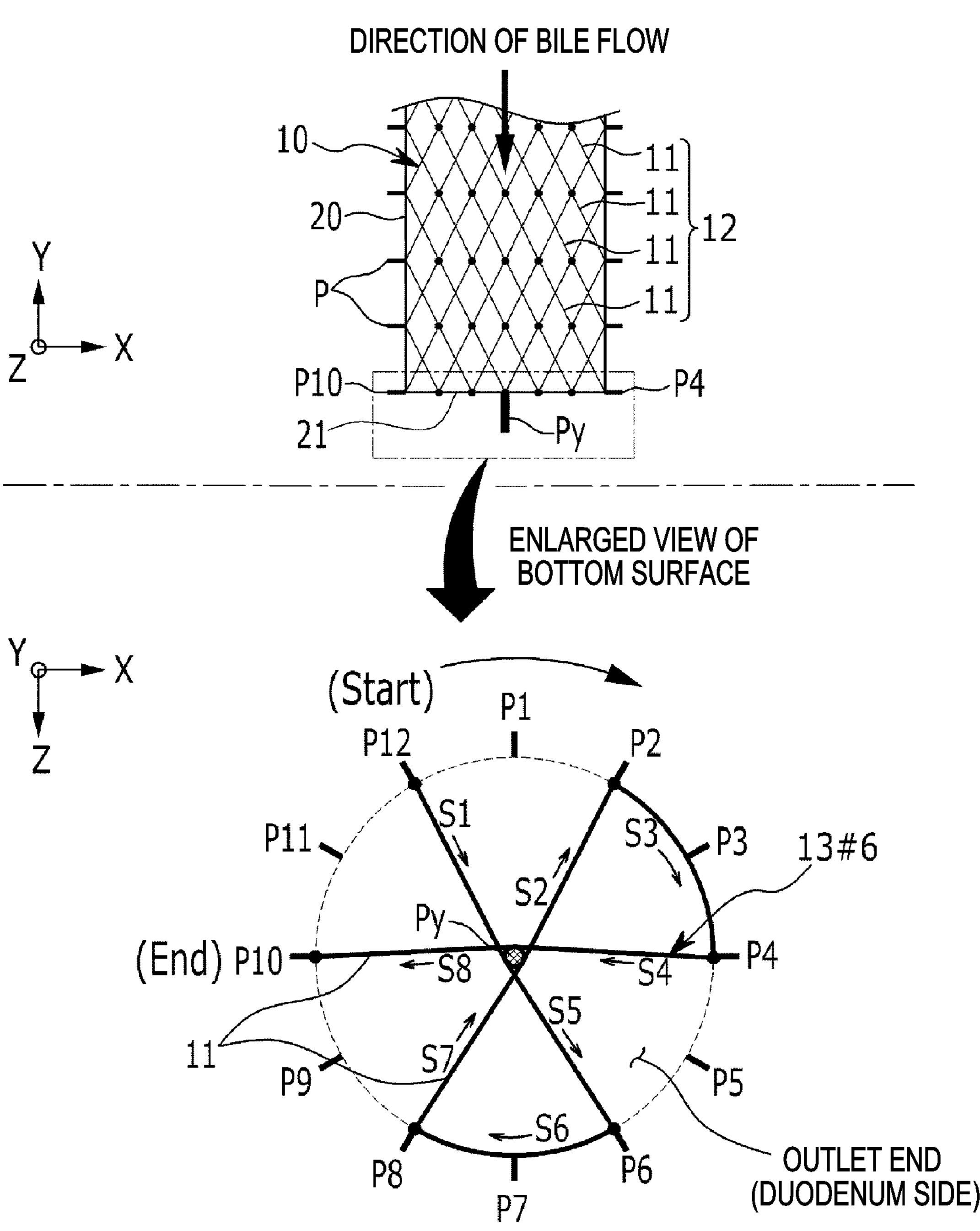
FIG. 8 illustrates a state in which a bile duct stent is manufactured using a jig having a vertical pin formed thereon according to a third embodiment of the present invention.

FIG. 8 illustrates a state in which a bile duct stent is manufactured using a jig having a vertical pin formed thereon according to a third embodiment of the present invention.

Hereinafter, since structures of a jig 20 and a stent 10 manufactured according thereto according to the third embodiment of the present invention are similar to those in the second embodiment described above, overlapping description will be omitted, and differences from the second embodiment will be mainly described.

Referring to FIG. 8, the jig 20 according to the third embodiment of the present invention includes at least one vertical pin Py formed on a lower surface 21 that corresponds to the outlet end (OUT) of the stent 10.

In the stent 10, the metal wires 11 are sequentially woven between the pins P, which are disposed in the circumferential direction X on the lower end of the jig 20, and the vertical pin Py to form a radial backflow-preventing pattern film 13#6 on the outlet end of the cylindrical body 12.

As a specific example, the radial backflow-preventing pattern film 13#6 is formed by, in the clockwise direction, the metal wire 11 being woven on the vertical pin Py at the center from a twelfth pin P12 which is a start point (Start) and then being woven on a second pin P2 and extending and moving to the fourth pin P4 in the circumferential direction X (steps S1, S2, and S3), and then being woven on the vertical pin Py at the center from the fourth pin P4 and then being woven on the sixth pin P6 and extending and moving to the eighth pin P8 in the circumferential direction X (steps S4, S5, and S6), and then being woven on the vertical pin Py at the center from the eighth pin P8 and then being woven on the tenth pin P10 which is an end point (End). Here, the steps S3 and S5 for extending and moving may be omitted according to changes in the manufacturing method, and a triangular line connecting a pair of pins and the vertical pin Py may be independently formed. Here, the metal wires 11 having the three reciprocating lines woven through the vertical pin Py may be fixed by intersecting each other in a bent state.

Meanwhile, the backflow-preventing pattern film 13 may be manufactured to be denser with an increase in the number of lines of the metal wire 11 that cross the outlet end (OUT). Thus, the backflow-preventing pattern film 13 is not limited to the radial backflow-preventing pattern film 13#6 described above and may be manufactured to have other dense radial backflow-preventing patterns according to various modifications.

Figure 9A:
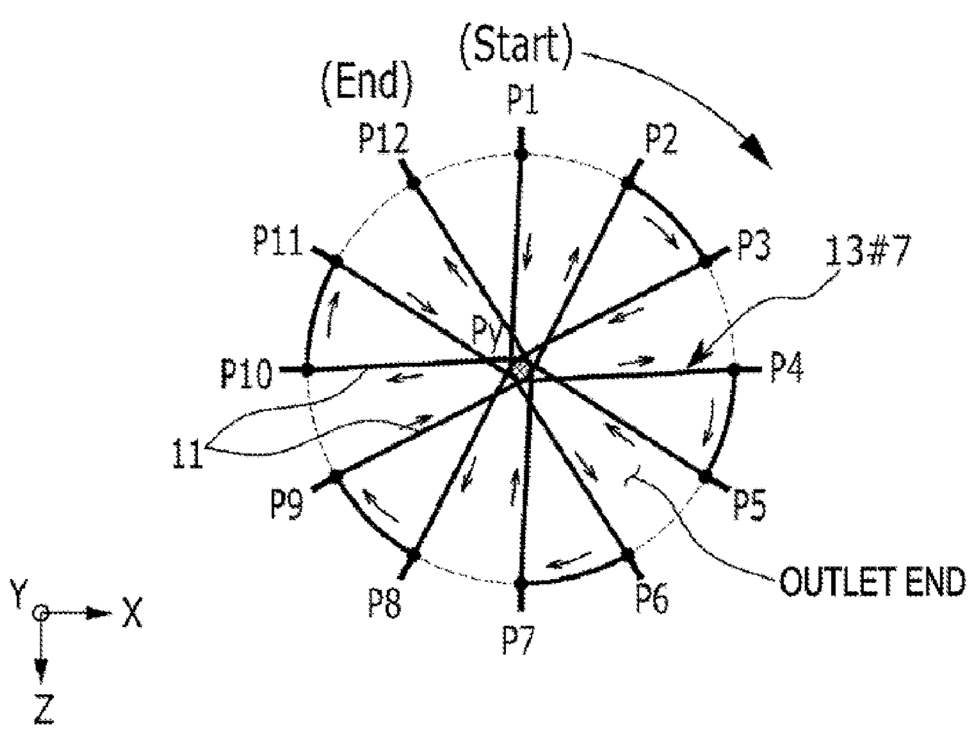
FIGS. 9A and 9B illustrate various forms of dense radial backflow-preventing pattern films according to the third embodiment of the present invention.
Figure 9B:
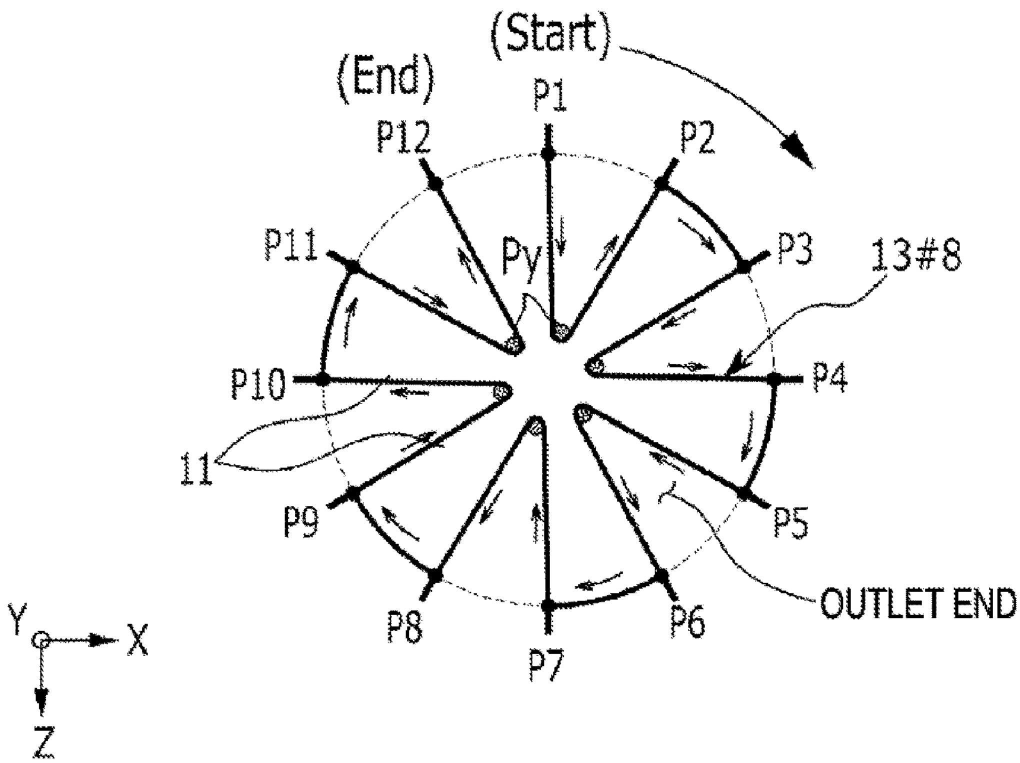

For example, FIGS. 9A and 9B illustrate various forms of dense radial backflow-preventing pattern films according to the third embodiment of the present invention.

First, referring to FIG. 9A, a first radial backflow-preventing pattern film 13#7 which is denser than the above-described radial backflow-preventing pattern film 13#6 due to an increase in the number of lines of the metal wire 11 woven on the vertical pin Py of the jig 20 of the stent 10 is shown.

Here, in the first radial backflow-preventing pattern film 13#7, the metal wires 11 are more densely sequentially woven between the pins P, which are disposed in the circumferential direction X on the lower end of the jig 20, and the vertical pin Py to form six reciprocating lines that are woven through the vertical pin Py. The six reciprocating lines may be woven with each other and fixed.

Next, referring to FIG. 9B, as a modification of the first dense radial backflow-preventing pattern film 13#7, a second radial backflow-preventing pattern film 13#8 is shown which is densely formed by a circular array of vertical pins Py being formed around the center of the lower surface 21 of the jig 20 and the metal wires 11 being woven therethrough.

That is, the metal wires 11 may be sequentially woven between six pins P, which are disposed in the circumferential direction X at the lower end of the jig 20, and the array of vertical pins Py corresponding thereto to form dense the second radial backflow-preventing pattern film 13#8 on the outlet end of the cylindrical body 12.

In this way, according to the third embodiment of the present invention, by utilizing at least one vertical pin Py formed on the lower surface 21 of the jig 20, there is an effect of allowing a radial pattern film, in which lines are denser and disposed at more uniform intervals as compared to the first and second embodiments, to be formed on the outlet end of the stent 10.

Meanwhile, optimal conditions for a bile duct stent in consideration of clinically important physical factors include high flexibility, an excellent radial expansile force, conformability with low axial force to allow the stent to maintain its shape while being bent along the flexion of the bile duct, minimization of a degree of shortening in order to place the stent at a correct position at a lesion site, reduction of a size of a cell between metal wires to reduce growth in a tumor, durability, and a high level of ease of loading the stent on a catheter which is a stent transfer system.

Among the above conditions, the ease of loading the stent on a catheter relates to loading the stent 10 in a diameter-reduced state on a catheter to facilitate placement of the stent 10. A structure in which it is difficult to physically reduce the diameter of the stent 10 has a disadvantage in that the level of ease of loading is low and a diameter of a catheter is increased, which makes it difficult to insert the catheter into the bile duct and adversely affects the operation carried out by a surgeon.

Here, the bile duct stent 10 according to the third embodiment of the present invention has a characteristic in that the radial backflow-preventing pattern films 13 of various shapes are formed by the metal wires 11 crossing the outlet end. Since such a characteristic may be disadvantageous for diameter reduction, the level of ease of loading the stent 10 on a catheter may be considered.

Thus, a bile duct stent 10 with a structure in which the level of ease of loading on a catheter is improved will be described next according to a fourth embodiment of the present invention.

Fourth Embodiment

Figure 10:
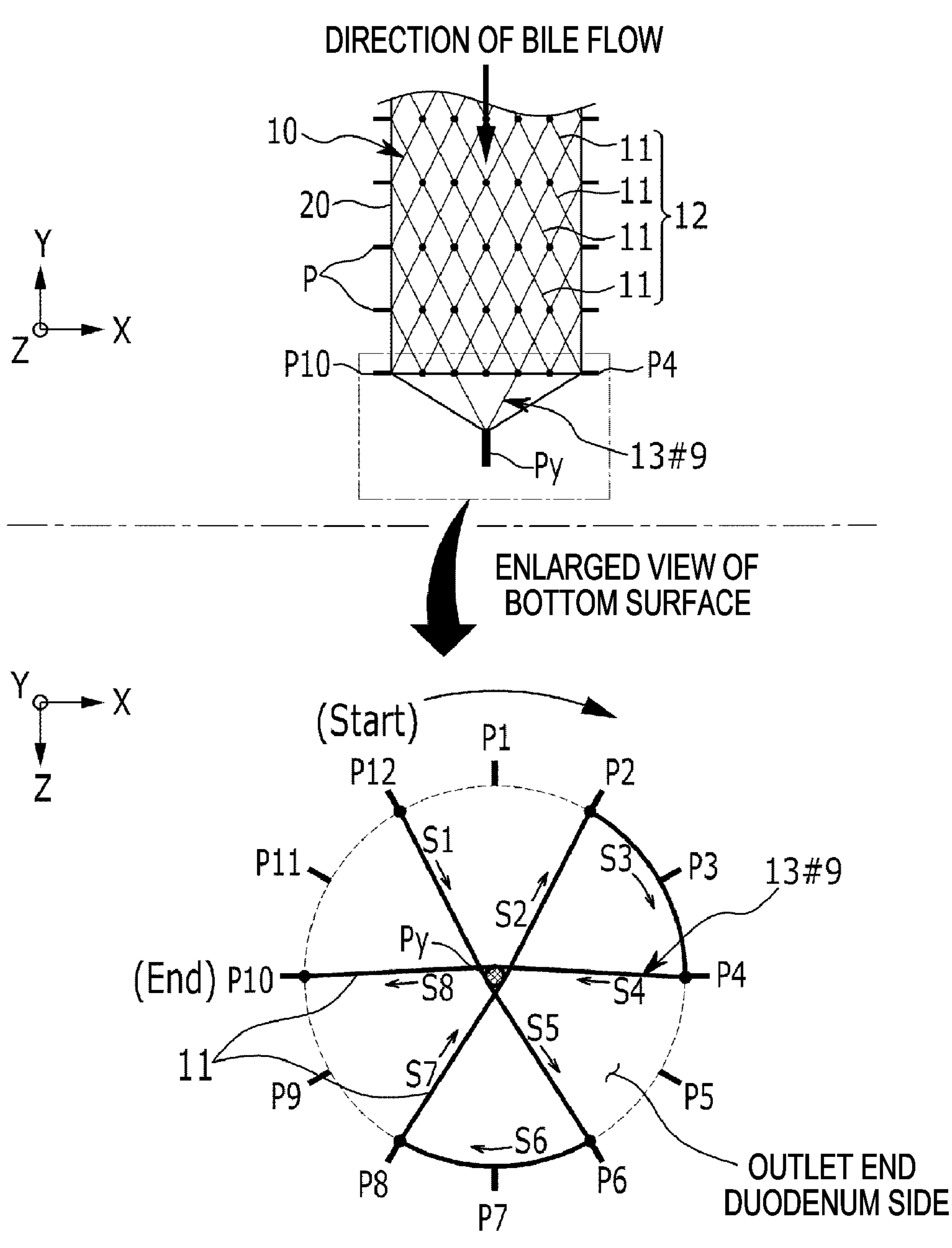
FIG. 10 illustrates a state in which a bile duct stent is manufactured using a conical jig according to a fourth embodiment of the present invention.

FIG. 10 illustrates a state in which a bile duct stent is manufactured using a conical jig according to a fourth embodiment of the present invention.

Figure 11:
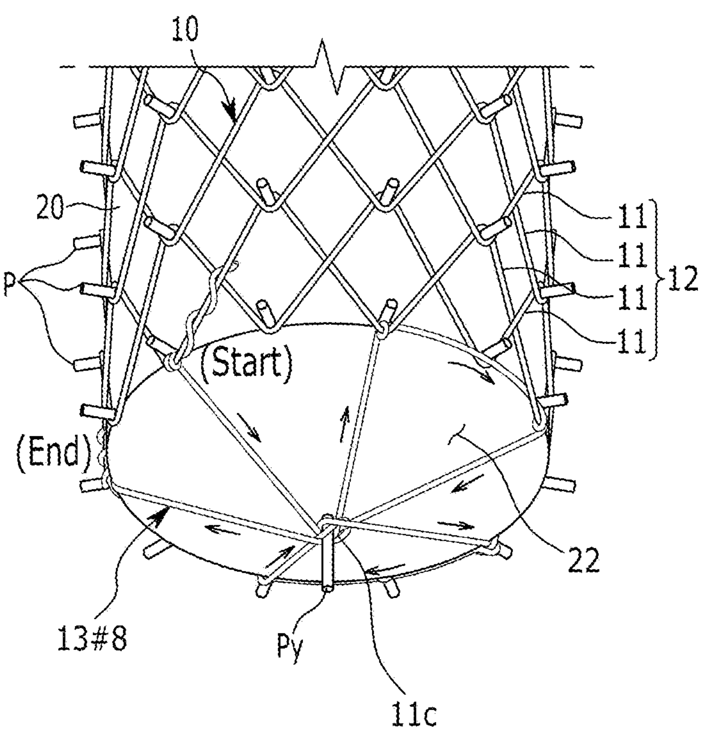
FIG. 11 is a perspective view illustrating a conical backflow-preventing pattern film according to the fourth embodiment of the present invention.

FIG. 11 is a perspective view illustrating a conical backflow-preventing pattern film according to the fourth embodiment of the present invention.

Hereinafter, since structures of a jig 20 and a stent 10 manufactured according thereto according to the fourth embodiment of the present invention are similar to those in the third embodiment described above, overlapping description will be omitted, and the structure in which the level of ease of loading on a catheter is improved will be mainly described.

Referring to FIGS. 10 and 11, the jig 20 according to the fourth embodiment of the present invention includes an outer peripheral surface 22, which is inclined in a conical shape at an outlet end (OUT) of the stent 10, and a vertical pin Py fixed to a vertex of the center of the outer peripheral surface 22.

Also, in the stent 10, a conical backflow-preventing pattern film 13#9 is formed in which the metal wires 11 are sequentially woven between the pins P, which are disposed in the circumferential direction X on the lower end of the jig 20, and the vertical pin Py to form a radial pattern, and the center protrudes due to the outer peripheral surface 22 inclined in the conical shape. For a specific method of weaving the metal wires 11 to form the conical backflow-preventing pattern film 13#9, the process of manufacturing the radial backflow-preventing pattern film 13#6 that has been described above with reference to FIG. 8 may be referenced. Further, the conical backflow-preventing pattern film 13#9 may be manufactured to have a denser structure by increasing the number of times the metal wires 11 are woven as in FIG. 9A.

Here, the lines of the metal wires 11 forming the conical backflow-preventing pattern film 13#9 form a triangular structure as bent portions 11*c* are formed due to the vertical pin Py and form an inclined structure in which the bent portions 11*c* intersect and radiate while interfering with each other.

Figure 12A:
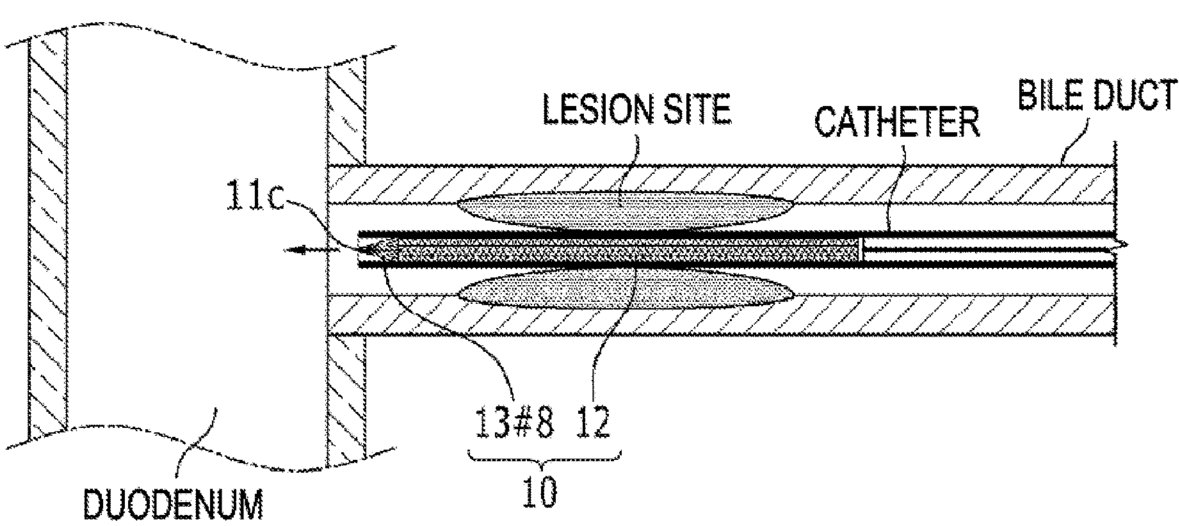
FIGS. 12A and 12B illustrate an example in which the stent according to the fourth embodiment of the present invention is placed at a lesion site of the bile duct.
Figure 12B:
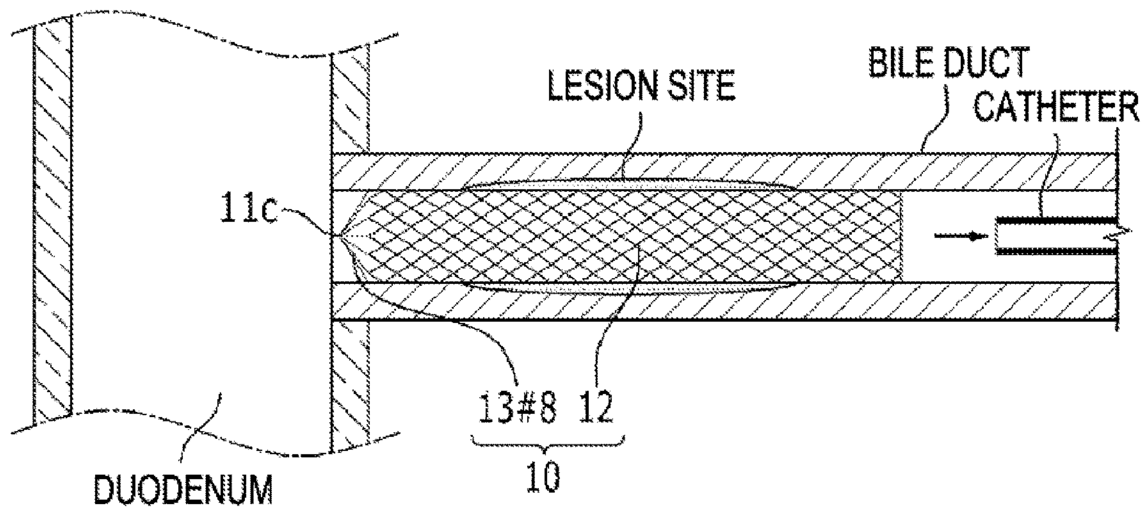

Meanwhile, FIGS. 12A and 12B illustrate an example in which the stent according to the fourth embodiment of the present invention is placed at a lesion site of the bile duct.

FIG. 12A shows a state in which the stent 10 according to the embodiment of the present invention is in a diameter-reduced state, loaded on a catheter, and moved past a lesion site in the bile duct.

Here, the conical backflow-preventing pattern film 13#9 is configured so that, when the stent 10 is loaded in an inner diameter of a catheter for stent placement, a diameter of the cylindrical body 12 is reduced due to an external pressure, and simultaneously, the bent portions 11*c* are folded without any physical resistance. Thus, there is an effect of facilitating loading of the stent 10 on the catheter.

Also, FIG. 12B shows a state in which the stent 10 exposed due to the catheter retracting is expanded, causing the lesion site in the bile duct to be expanded.

Here, the conical backflow-preventing pattern film 13#9 is expanded at a duodenum-side passage of the bile duct to prevent the backflow of food from the duodenum into the bile duct and discharge bile, which flows in the bile duct, to the duodenum.

Figure 13:
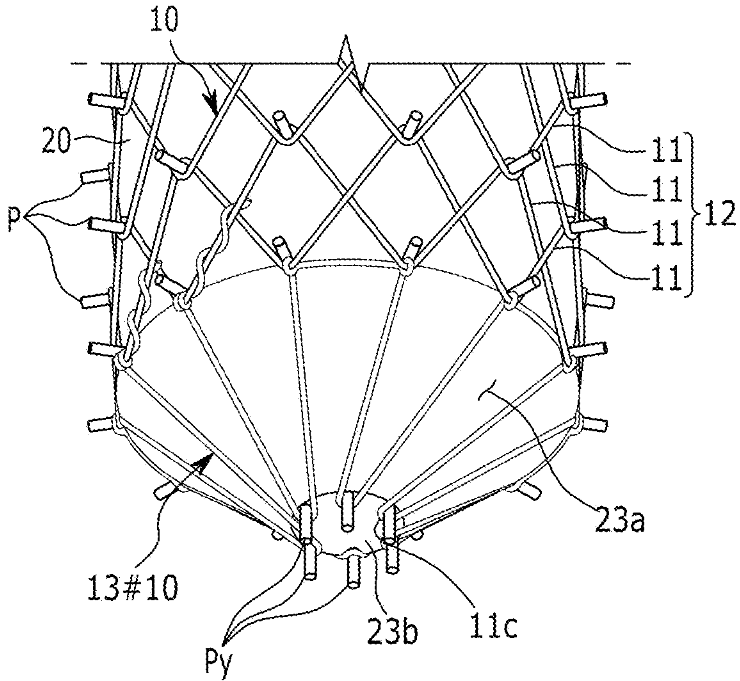
FIG. 13 is a perspective view illustrating a truncated conical backflow-preventing pattern film according to the fourth embodiment of the present invention.

Meanwhile, FIG. 13 is a perspective view illustrating a truncated conical backflow-preventing pattern film according to the fourth embodiment of the present invention.

Referring to FIG. 13, the jig 20 according to the fourth embodiment of the present invention includes a truncated cone outer peripheral surface 23*a*, which is inclined, and a truncated cone lower surface 23*b* formed at an outlet end (OUT) of the stent 10 in order to constitute a truncated conical structure which is broad at the top and gets narrower toward the bottom and also includes a circular array of vertical pins Py formed around the center of the truncated cone lower surface 23*b*.

Here, in the stent 10, by the metal wires 11 being sequentially woven between the pins P, which are disposed in the circumferential direction X at the lower end of the jig 20, and the array of vertical pins Py which correspond to the pins P and are arranged in a circular shape on the truncated cone lower surface 23*b*, a truncated conical backflow-preventing pattern film 13#10 may be formed on the outlet end of the cylindrical body 12.

Here, in each of the lines of the metal wires 11 constituting the truncated conical backflow-preventing pattern film 13#10, the bent portion 11*c* may be formed due to the vertical pin Py, and the bent portions 11*c* may radiate and form an inclined structure without interfering with each other.

In this way, according to the embodiments of the present invention, by forming various backflow-preventing pattern films using a pattern member made of threads or metal wires at a duodenum-side outlet end of a cylindrical body of a bile duct stent, there is an effect of preventing the backflow of food into the stent (the bile duct).

Also, backflow-preventing pattern films of various dense patterns can be easily manufactured with a single line of thread or metal wire on an outlet end of the bile duct stent, and by configuring the backflow-preventing pattern films using nylon threads or metal wires, there is an effect of securing durability.

In addition, by forming a radial backflow-preventing pattern film, which has a bent portion formed at the center, using metal wires having a self-expansile force, there is an effect of facilitating diameter reduction of the bile duct stent when loading the bile duct stent on a catheter. Further, there is an effect of allowing the backflow preventing performance to be maintained regardless of whether any deformation occurs in the cylindrical body of the stent due to a pressure in a lesion site.

Advantageous Effects

According to embodiments of the present invention, by forming various backflow-preventing pattern films using a pattern member made of threads or metal wires at a duodenum-side outlet end of a cylindrical body of a bile duct stent, there is an effect of preventing the backflow of food into the stent (the bile duct).

Also, backflow-preventing pattern films of various dense patterns can be easily manufactured with a single line of thread or metal wire on an outlet end of the bile duct stent, and by configuring the backflow-preventing pattern films using nylon threads or metal wires, there is an effect of securing durability.

In addition, by forming a radial backflow-preventing pattern film, which has a bent portion formed at the center, using metal wires having a self-expansile force, there is an effect of facilitating diameter reduction of the bile duct stent when loading the bile duct stent on a catheter. Further, there is an effect of allowing the backflow preventing performance to be maintained regardless of whether any deformation occurs in the cylindrical body of the stent due to pressure on a lesion site.

The embodiments of the present invention are not implemented only through the device and/or method described above and may be implemented through programs for realizing functions corresponding to configurations of the embodiments of the present invention, recording media in which the programs are recorded, etc. Such implementations may be easily carried out by those of ordinary skill in the art to which the present invention pertains from the above description of the embodiments.

The embodiments of the present invention have been described in detail above, but the scope of rights of the present invention is not limited thereto, and various modifications and improvements made by those of ordinary skill in the art using the basic concept of the present invention defined in the attached claims also fall within the scope of rights of the present invention.

What is claimed is:

1. A bile duct stent comprising:

a cylindrical body having a mesh structure formed by zigzagging metal wires of a shape memory alloy; and a backflow-preventing pattern film disposed at an outlet end of the cylindrical body, the backflow-preventing pattern film comprising metal wire lines crossing an outlet opening one time or more to form a network structure, wherein the backflow-preventing pattern film forms a radial network structure in which the metal wire lines extend between an outer peripheral region adjacent the outlet end and a center region so as to form a radial pattern, and wherein the radial backflow-preventing pattern film comprises at least three reciprocating line segments of the metal wire lines, each reciprocating line segment passing through the center region and returning toward the outer peripheral region, wherein, at the center region, bent portions are formed in the metal wire lines and multiple ones of the metal wire lines are mechanically fixed by intersecting each other in a bent state, wherein bent portions of at least three of the reciprocating line segments overlap with one another at a common central point to define a single overlapped central hub region, wherein the overlapped central hub region defines a central opening located at the center region, the central opening corresponding to a position at which a vertical pin (Py) is temporarily disposed during formation of the radial backflow-preventing pattern film and absent in a final product, such that the bent portions remain superposed around the central opening and are mechanically fixed to one another at the central hub region, wherein the metal wire lines are self-expansile such that, when the bile duct stent is loaded in an inner diameter of a catheter for stent placement and a diameter of the cylindrical body is reduced by an external pressure, the bent portions fold to facilitate loading of the bile duct stent on the catheter, and wherein the radial backflow-preventing pattern film is configured to maintain backflow-preventing performance irrespective of deformation of the cylindrical body due to pressure at a lesion site.

2. The bile duct stent of claim 1, wherein the backflow-preventing pattern film is finished with a twist knot after one line of metal wires is continuously woven from a start-point position to an end-point position via at least one intermediate position.

* * * * *